United States Patent
Singh Sachdeva et al.

(10) Patent No.: US 11,707,439 B2
(45) Date of Patent: Jul. 25, 2023

(54) PARENTERAL TREATMENTS INVOLVING AMINOADAMANTANE DERIVATIVES

(71) Applicants: Gurpartap Singh Sachdeva, Princeton Junction, NJ (US); Suresh Borsadia, Plainsboro, NJ (US); Kalpana Patel, West Windsor, NJ (US); Krunal Raval, Gujarat (IN)

(72) Inventors: Gurpartap Singh Sachdeva, Princeton Junction, NJ (US); Suresh Borsadia, Plainsboro, NJ (US); Kalpana Patel, West Windsor, NJ (US); Krunal Raval, Gujarat (IN)

(73) Assignee: Shinkei Therapeutics, Inc., Princeton, NJ (US)

( * ) Notice: Subject to any disclaimer, the term of this patent is extended or adjusted under 35 U.S.C. 154(b) by 397 days.

(21) Appl. No.: 16/840,561

(22) Filed: Apr. 6, 2020

(65) Prior Publication Data

US 2020/0315991 A1     Oct. 8, 2020

Related U.S. Application Data

(60) Provisional application No. 62/830,830, filed on Apr. 8, 2019.

(51) Int. Cl.
*A61K 31/13*     (2006.01)
*A61K 45/06*     (2006.01)
*A61K 9/00*      (2006.01)

(52) U.S. Cl.
CPC ............ *A61K 31/13* (2013.01); *A61K 9/0019* (2013.01); *A61K 45/06* (2013.01)

(58) Field of Classification Search
CPC ....... A61K 31/13; A61K 45/06; A61K 9/0019
See application file for complete search history.

(56) References Cited

U.S. PATENT DOCUMENTS

| | | | |
|---|---|---|---|
| 7,943,632 B2 | 5/2011 | Katzman et al. | |
| 2006/0089373 A1* | 4/2006 | Katzman ............ | A61K 31/4745 514/295 |

OTHER PUBLICATIONS

PK-Merz® Infusion, Physician's Prescribing Information. (Year: 2022).*

(Continued)

*Primary Examiner* — Jean P Cornet
(74) *Attorney, Agent, or Firm* — Wiliam D. Hare, Esq.; McNeely, Hare & War, LLP

(57) ABSTRACT

A method and composition is described for treating impaired neurological function, CNS disease or condition, including altered state of consciousness disorders in a human subject, comprising parenterally administering a composition comprising aminoadamantane derivatives or salts thereof, alone or in combination with other neuroprotective and/or anti-inflammatory compounds, in a pharmacologically effective amount. In some embodiments, a method for treating traumatic brain injury caused by a stroke or an accident in a human subject is provided comprising intravenously administering a composition comprising amantadine hydrochloride in a pharmacologically effective amount to the subject in need thereof.

20 Claims, No Drawings

(56) References Cited

OTHER PUBLICATIONS

Brenner, J Neurol (1989) 236: 153-156, (Year: 1989).*
Prescribing Information, Baxter Corporation, 2018. (Year: 2018).*
E.A. Fridman et al., Continuous subcutaneous apomorphine for severe disorders of consciousness after traumatic brain injury, Brain Injury, Apr. 2010; 24(4): 636-641.
J.T. Giacino et al., Placebo-Controlled Trial of Amantadine for Severe Traumatic Brain Injury, The New England Journal of Medicine, Mar. 1, 2012; 366:819-26.
Eagle Yi-Kung Huang et al., Amantadine Ameliorates Dopamine-Releasing Deficits and Behavioral Deficits in Rats after Fluid Percussion Injury, PLoS ONE 9(1): e86354. doi:10.1371/journal.pone.0086354, Jan. 2014.
J. Kornhuber et al., Pharmacokinetic Characterization of Amantadine in Human Brain Tissue, Ther Drug Monit 2006; 28:693-695.
J. Kornhuber et al., Therapbeutic Brain Concentration of the NMDA Receptor Antagonist Amantadine, Neuropharmacology vol. 34, No. I, pp. 713-721, 1995.
M.F. Kraus et al., Effects of the dopaminergic agent and NMDA receptor antagonist amantadine on cognitive function, cerebral glucose metabolism and D2 receptor availability in chronic traumatic brain injury: A study using positron emission tomography (PET), Brain Injury, Jul. 2005; 19(7): 471-479.
S.M. Lehnerer et al., Awakening with amantadine from a persistent vegetative state after subarachnoid haemorrhage, BMJ Case Rep 2017. doi:10.1136/bcr-2017-220305.
B. Saniova et al., The outcome of patients with severe head injuries treated with amantadine sulphate, J Neural Fransm (2004) 111: 511 514, DOI 10.1007/s00702-004-0112-4.
O. Gosseries et al., Amantadine, Apomorphine and Zolpidem in the Treatment of Disorders of Consciousness, Current Pharmaceutical Design, 2014, 20, 4167-4184.
J.M. Meythaler, Amantadine to Improve Neurorecovery in Traumatic Brain Injury-Associated Diffuse Axonal Injury: A Pilot Double-blind Randomized Trial, J Head Trauma Rehabil 2002;17(4):300-313.
E.A. Fridman, Continuous subcutaneous apomorphine for severe disorders of consciousness after traumatic brain njury, Brain Injury, Apr. 2010; 24(4): 636-641.
J.T. Giacino et al., Placebo-Controlled Trial of Amantadine for Severe Traumatic Brain Injury, N Engl J Med 2012;366:819-26.
Gocovri(tm) Prescribing Information, issued Aug. 2017.
Osmolex ER Prescribing Information, issued Feb. 2018.
PK-Merz Infusion Physician's Prescribing Information, approved Nov. 2009.
Symmetrel(r) (Amantadine Hydrochloride, USP) Tablets and Syrup Prescribing Information, Jan. 2009.

* cited by examiner

PARENTERAL TREATMENTS INVOLVING AMINOADAMANTANE DERIVATIVES

FIELD OF THE INVENTION

The invention relates to new therapeutic techniques involving aminoadamantane derivatives. Particularly, the present invention relates to use of aminoadamantane derivatives for use in the treatment of impaired neurological function, central nervous system (CNS) disease or condition. Particularly, the present invention provides a parenteral composition for the treatment of traumatic brain injury, using amantadine or a pharmaceutically acceptable salt thereof.

BACKGROUND

There are several mechanisms of brain injury like open head injury, closed head injury, deceleration injury. Various causes of traumatic Brain Injury (TBI) include falling down, vehicle accidents, public or domestic violence, explosions, sport injuries, combat injuries and the like. The complications arising out of TBI include altered consciousness, seizures, fluid buildup, infections, blood vessel damage, nerve damage, cognitive problems, communication problems, sensory deficits, emotional and behavioural problems, and the like. TBI requires rapid diagnosis. Often, it is important to begin treatment within the "golden hour" following injury. TBI can have wide-ranging physical and psychological effects. Some signs or symptoms may appear immediately after the traumatic event, while others may appear days or weeks later.

TBI can be largely divided into two types—(i) mild traumatic brain injury, and (ii) severe traumatic brain injury (sTBI). The signs and symptoms of mild traumatic brain injury may include—(1) physical symptoms, such as loss of consciousness for a few seconds to a few minutes, feeling confused or disoriented, headache, nausea or vomiting, fatigue or drowsiness, problems with speech, dizziness or loss of balance; (2) sensory symptoms, such as blurred vision, ringing in the ears, a bad taste in the mouth or changes in the ability to smell, sensitivity to light or sound; (3) cognitive or mental symptoms, such as memory or concentration problems, mood changes or mood swings, feeling depressed or anxious. The signs and symptoms of moderate to severe TBI can include any of the signs and symptoms of mild injury, as well as symptoms that may appear within the first hours to days after a head injury, such as (1) physical symptoms such as loss of consciousness from several minutes to hours, persistent headache or headache that worsens, repeated vomiting or nausea, convulsions or seizures, dilation of one or both pupils of the eyes, clear fluids draining from the nose or ears, inability to awaken from sleep, weakness or numbness in fingers and toes, loss of coordination; (2) cognitive or mental symptoms, such as profound confusion, agitation, combativeness or other unusual behavior, slurred speech, coma and other disorders of consciousness. Moderate to severe traumatic brain injury can result in prolonged or permanent changes in a person's state of consciousness, awareness or responsiveness. Different states of consciousness, typically referred to as altered consciousness or disorders of consciousness, include coma, vegetative state and minimally conscious state. TBI can also lead to cognitive problems, communication problems, social and behavioral problems, emotional and sensory problems.

Medications are typically used to help control symptoms, such as sedatives, pain killers, diuretics, anti-seizure medications, which help physicians to manage the patient well. Different therapeutic interventions have been proposed to aid the functional recovery of post-traumatic coma patients, but the results have been inconclusive. Various pharmacological agents have been suggested in literature for treating TBI patients, such as using oral formulations of levodopa and carbidopa (Haig et al., Arch. Phys. Med Rehabil., 71: 1081-1083 (1990)), bromocriptine (Passler et al., Arch. Phys. Med. Rehab., 82: 311-315 (2001)), methylphenidate (Whyte et al., J. Head Trauma Rehabil., 17(4): 284-299 (2002)), and amantadine (Wolfand Gleckman, Brain Injury, 9(5): 487-493 (1995); Meythaler et al., J. Head Trauma Rehabil., 17(1): 300-314 (2002)).

Aminoadamantane derivatives are weak antagonists of the N-methyl-D-aspartate (NMDA) receptors with neuroprotective properties, and are known to increase dopamine release and block dopamine reuptake (Kornhuber et al., J Neural Transm Suppl., 43:91-104 (1994); Peeters et al., *Brain Res.,* 949:32-41 (2002); and Rogawski et al., *CNS Drug Rev.,* 9(3):275-308 (2003)). Aminoadamantanes also bind to and act as agonists of the al receptors (Peeters et al., *Eur J Neurosci.,* 19(8):2212-2220 (2004)). Aminoadamantane derivatives currently in use include amantadine (1-amantanamine), adapromine (1-adamantanylpropylamine), rimantadine (methyl-1-adamatanethylamine), bromantane (1-amino-2-bromophenyladamantane), and memantine (3,5-dimethyl-1-adamantanamine). Amantadine is approved for the treatment of idiopathic Parkinson's disease, post-encephalitic Parkinsonism, symptomatic Parkinsonism following injury to the nervous system by carbon monoxide intoxication, Parkinsonism which develops in association with cerebral arteriosclerosis in elderly patients, and dyskinesia resulting from treatment with levodopa for Parkinson's disease. Amantadine has also been reported to be moderately effective for multiple sclerosis related fatigue (Braley et al., *Sleep,* 33(8):1061-1067(2010)). Amantadine decreases the toxic effects of the glutamatergic neurotransmitter system which plays an important role in many psychiatric disorders and has been reported for its beneficial effects in treating attention deficit hyperactivity disorder (ADHD), resistant depression, obsessive compulsive disorder, controlling the symptoms of irritability and hyperactivity in autistic disorder, controlling agitation and aggression in traumatic brain injury, and in counteracting side effects of some psychotropic medications (Hosenbocus et al., J Can Acad Child Adolesc Psychiatry., 22(1):55-60 (2013)). Amantadine is well tolerated in children and adolescents. Id. Rimantadine has been used for the treatment of Parkinson's disease (Singer et al., Mov Disord., 20(7):873-7 (2005)). Memantine is used to treat moderate-to-severe Alzheimer's disease (Mount et al., *Nat. Med.,* 12(7):780-4 (2006)). Bromantane is an atypical psychostimulant and anxiolytic drug used in the treatment of neurasthenia (Neznamov et al., *Zh Nevrol Psikhiatr Im S S Korsakova* (in Russian), 109(5):20-6 (2009)). Currently known aminoadamantane derivatives are administered orally to human subjects, but none of them has been approved for use in treating TBI.

Gosseries et al, Current Pharm. Design, 20, 4167-4184 (2014) is a review article which reports that amantadine hydrochloride has been used as a parenteral formulation in the treatment of dyskinetic patients with Parkinson's disease (See also PK-Merz infusion approved in Germany for the treatment of parkinsonism that does not respond to oral therapy, which includes Parkinson's syndromes and decreased vigilance), and as oral administration through NG feeding tubes in post-comatose patients for decreasing agitation and for promoting recovery of consciousness. However, Gosseries et al mentions that the early clinical trials, which suggested positive therapeutic effects on cognitive function, arousal level and agitation in patients with TBI, were solely based on physicians' observations, and none of them employed standardized measures or a placebo as control. In fact, the authors ask the readers to exercise caution while using high doses of amantadine, and to look for side effects, such as pedal edema, hypomania, generalized seizure, visual hallucinations, especially in patients with chronic TBI. They also state that many studies were not defined as to the state of the patients and comparisons were wrong, thereby making most studies inconclusive. Some studies indicated general improvement upon use of amantadine, but reported there to be no difference over placebo with respect to neuropsychological outcome. Gosseries et al in fact mentions that since dopamine levels vary from patient to patient, it is difficult to treat patients with definitive outcome, and with defined dose and regime.

Giacino et al, (N Engl J Med., 366, 819-826 (2012)) reported a placebo-controlled trial of amantadine for severe traumatic brain injury, wherein patients were dosed with Symmetrel, the oral tablet and syrup formulations, approved for use in influenza. While the authors report that their findings suggest that amantadine can be used safely at daily oral doses of 200 mg to 400 mg in patients with severe TBI, they also cite limitations of their study as—(1) the sample comprised patients admitted to inpatient rehabilitation centers, raising the possibility of selection bias because decisions about admission to a rehabilitation center may be influenced by the probability of further improvement, (2) the findings do not address the effects of prolonged treatment on long-term outcomes, and (3) the study did not restrict standard rehabilitation interventions, so one cannot determine the degree to which the benefits of amantadine are independent of or synergistic with such standard treatments. Thus, the authors conclude—"Whether treatment with amantadine, as compared with placebo, improves the long-term outcome or simply accelerates recovery en route to an equivalent level of function remains unknown". Finally, the authors state that future research should focus on determining the pathophysiological characteristics of patients who have a response to amantadine, the most effective dosage and duration of treatment, and timing of its initiation.

Kornhuber, J. et al, Neuropharmacology Vol. 34, No. I, pp. 713-721 (1995) states that while the NMDA receptor antagonistic effects explain the therapeutic effects of amantadine in idiopathic Parkinson's disease, drug-induced extrapyramidal symptoms and neuroleptic malignant syndrome, and while it is possible that it is the low affinity and associated fast voltage-dependent channel blocking kinetics that is responsible for the better tolerability of amantadine, there are no reported details on levels of amantadine in cerebrospinal fluid (CSF). The authors conducted a rat study to establish the same. However, they do not discuss the use of amantadine in the treatment of TBI, or treatment of any diseases with altered consciousness. Yet another publication by Kornhuber, J. et al in Ther. Drug Monit., Volume 28, Number 5, 693-695 (2006), reports population pharmacokinetic analysis on the basis of data taken from a previous investigation, in which amantadine concentrations were measured in different areas of postmortem brain tissue taken from 21 patients previously treated with amantadine sulfate. The authors assumed that a single daily dose of 200 mg amantadine was administered to the mean subject during the treatment period, followed by a drug-free interval. The authors state that the elimination half-life of amantadine from brain tissue is much longer than from blood and is comparable to the previously investigated neuroleptic drugs haloperidol and levomepromazine. Therefore, they state that the clinical relevance of this long elimination half-life is not clear at present and should be further investigated.

Lehnerer S M, et al. BMJ Case Rep, 1-4 (2017) reported the single case of a 36-year-old woman with a subarachnoid haemorrhage (SAH) caused by a rupture of a right-sided middle cerebral artery aneurysm and subsequent malignant infarction of the right hemisphere leading to a persistent vegetative state and severe spastic tetraparesis with recurrent myoclonic, wherein amantadine treatment resulted in stunning awakening of the patient, fully orientated within days. In this single isolated case, the patient was treated with amantadine, starting with 100 mg/day intravenously, increasing the dose 100 mg per day, and switched to an enteral drug administration after reaching the maximum dose of 300 mg/day given once in the morning. Essentially therefore, the amantadine therapy to this patient was through oral administration of amantadine. The authors conclude that their findings warrant trials to investigate amantadine in the treatment of unresponsive wakefulness syndromes due to acute central nervous system diseases.

Fridman E A et al, Brain Injury, 24(4): 636-641 (2010) reported a prospective open-labelled clinical study to test the feasibility, relative efficacy and safety of continuous subcutaneous administration of apomorphine in Vegetative State (VS) or Minimally Conscious State (MCS) patients due to severe traumatic brain injury. Because of the known emetic effects of apomorphine, 2 days prior to the initiation of apomorphine treatment, patients received 20 mg t.i.d. of domperidone, a peripherally acting dopamine antagonist that does not cross the blood-brain barrier and therefore does not interfere with the CNS activity of apomorphine. Fridman reports that continuous subcutaneous apomorphine has been used extensively and safely for many years to treat patients with Parkinson's disease (PD), but the most common side-effects reported in the PD population that are of concern in VS and MCS patients are: skin nodules at the site of injection, nausea/vomiting and, in less than 5% of PD patients, eosinophilia and orthostatic hypotension. Clearly, these are detrimental in patients with TBI, as it will impact the overall condition of the patient, and worsen recovery. Based on this clinical study, Fridman et al also secured a patent, U.S. Pat. No. 7,943,632, which claims a method of treating an altered consciousness state (ACS) in an individual who has sustained a traumatic brain injury comprising administering to said individual an effective amount of apomorphine. While literature reports a variety of dopamine receptor agonists, which include without limitation, apomorphine, bromocriptine, amantadine, pergolide, pramipexole, ropinirole, fenoldopam, cabergoline, rotigotine, lysuride, talipexale, 7-OHDPAT, quinpirole, and SKF-38393, Fridman et al argue that apomorphine is the most potent and effective of these in treating altered consciousness state. They merely suggest use of amantadine as an additional, optional dopaminergic agent with apomorphine.

Huang et al, PLOS One, 9(1), e86354 (2014) investigated the role of dopamine in cognitive and motor learning skill deficits after a traumatic brain injury (TBI). The authors investigated dopamine release and behavioral changes at a series of time points after fluid percussion injury in rats, and explored the potential of amantadine hydrochloride as a chronic treatment to provide behavioral recovery. Chronic amantadine therapy reversed dopamine-release deficits, and behavioral impairment after fluid percussion injuries were ameliorated in the rats treated by using amantadine-pumping infusion. The authors report—"To date, no studies have explored the potential of amantadine hydrochloride for providing behavioral recovery in chronic treatments. Nor has the mechanism of amantadine therapy been studied by focusing on its effects on bursting and tonic dopamine release after injury, which can provide a direct reversal of dopamine release and result in improved motorfunctions." The authors state that variations in dopamine levels after TBI have been shown in previous reports and are shown in their data as well, but these data seem inconsistent and controversial as they may indicate alterations in dopamine biosynthesis, reuptake, and degradation after TBI. The rat study conducted by Huang et al provides data showing that the suppression of dopamine release after TBI was ameliorated by chronic infusion of the amantadine; this phenomenon may also be due to dopamine neuron protection after TBI as well as due to inhibition of the reuptake of dopamine by amantadine infusion. The findings of Huang et al suggest that chronic amantadine therapy accelerates recovery in cognitive and motor deficits after fluid percussion injury, which is consistent with the results from previous reports, and therefore, the reversal of dopamine release changes and the improvement in behavioral deficits caused by chronic infusion of amantadine could possibly provide value in chronic therapy for treating severe TBI. However, the authors do not provide any details on the use in humans, nor any details on the dose, the regimen to follow and/or the results in human patients with TBI.

Saniova, B., J Neural Transm, 111: 511-514 (2004) discusses the outcome of patients with severe head injuries treated with amantadine sulphate. In the group of patients with severe brain injuries treated with standard therapy plus amantadine sulphate (group 1 patients received amantadine sulphate in a dose of 200 mg i.v. twice daily for 3 days, starting on day 3 of hospitalization) the outcome Glasgow Coma Scale was higher and the case fatality rate lower than in the group treated with standard therapy alone. The authors state—"We are aware, that this is a retrospective study analysing a small series open to bias and we consider it as a pilot study that will serve as a basis for future prospective, randomised studies." Saniova et al do not provide any details on the formulation to be used, the regime to follow (the reported data is around administration of amantadine for 3 days only), rate of infusion and/or any other details on use of amantadine in TBI patients.

Several other such reports for off-label use of amantadine in patients with TBI have been reported. Chandler M C et al, Brain Injury 2: 309-311 (1988) reported two cases of recovering brain injury patients with difficult-to-treat destructive behavior, whose agitation and aggression responded to amantadine. The authors concluded that direct-acting dopamine agonists such as amantadine may be the preferred treatment for patients with behavior problems in the acute stages of recovery from coma. Kraus M F, Brain Injury, 19(7): 471-479 (2005) reported a study that was performed to assess effects of amantadine on chronic TBI. The primary hypotheses were that amantadine treatment would result in executive function improvement and increased activity in pre-frontal cortex. This study provides the first known data on the use of PET and cognitive testing to assess the effects of amantadine, and suggests potential neurobiological substrates for amantadine activity. Clinically, amantadine provides a potentially effective and well-tolerated option for treating aspects of executive dysfunction following TBI, as per Kraus et al. But the authors recommend further studies of amantadine and related compounds in the treatment of TBI.

Thus, parenteral administration may quickly and effectively treat or control central nervous system (CNS) disease progression, especially in patients who find it difficult to swallow or are unable to swallow, patients with cognitive impairment, and patients who are unconscious, such as in case of TBI.

However, despite all these reports spanning over more than two decades, there are no approved medications for the treatment of the major conditions arising out of TBI, as yet. Specifically, while the oral amantadine products (approved for use in influenza), and the IV product (approved for use in Parkinson's disease), have been tried in TBI patients, such use of amantadine in this off-label indication, at most, may only provide a motivation to conduct additional studies. The contradictory reports on efficacy, the side effects reported, the various reports from oral and IV administration, and the preferred use of apomorphine over amantadine by some researchers, only further complicates the situation—not to mention that many are concerned if a dopaminergic agent is in fact to be administered in TBI patients, who already may have high levels of dopamine post the injury, thereby leading to excitotoxic disruption.

Traumatic or ischemic injuries to the CNS, such as TBI, initiate reactive biochemical changes, some of which are autodestructive and others neuroprotective. Identification of these endogenous factors and their regulation has not been easy, and is perhaps one of the reasons why there is no approved medication for the treatment of patients with TBI.

SUMMARY

The present invention relates to methods for treating a CNS disease or condition in a human subject comprising parenterally administering a composition comprising an aminoadamantane derivative or a salt thereof in a pharmacologically effective amount to the subject in need thereof.

In some embodiments, the aminoadamantane derivative is amantadine, rimantadine, memantine, adapromine, bromantane or their pharmaceutically acceptable salts, or a mixture thereof. In a preferred embodiment, the aminoadamantane derivative is amantadine hydrochloride.

In some embodiments, the CNS disease or condition is Parkinson's disease, Parkinsonism, multiple sclerosis, Alzheimer's disease, posttraumatic stress disorder (PTSD) and/or traumatic brain injury. In preferred embodiments, the CNS condition is traumatic brain injury caused by, among others, a stroke, an accident or asphyxiation.

Some embodiments of the present invention are compositions of aminoadamantane derivatives that are used for treating TBI, which includes mild TBI, severe TBI, and various conditions arising out of severe TBI, such as coma, vegetative state, minimum conscious state and disorder of consciousness.

In some embodiments, a method of treating a traumatic brain injury caused by a stroke, an accident or asphyxiation in a human subject is provided, comprising parenterally administering a composition comprising amantadine hydrochloride in a pharmacologically effective amount to the subject in need thereof.

In preferred embodiments, the amantadine hydrochloride is administered by intravenous route to a patient with TBI.

In one embodiment, the amantadine hydrochloride is present in the parenteral composition in an amount ranging from about 50 mg to about 500 mg.

In yet another embodiment, the daily dose of amantadine hydrochloride is about 200 mg.

In still another embodiment, the daily dose of amantadine hydrochloride is about 300 mg.

In yet another embodiment, the daily dose of amantadine hydrochloride is about 400 mg.

Some embodiments of the present invention provide the daily dose of amantadine hydrochloride divided into two or more doses. In preferred embodiments, the total daily dose of amantadine hydrochloride may be intravenously administered to a patient with TBI as a single dose, or as two doses or may be administered as three doses per day.

In one embodiment, the composition is in the form of a solution of amantadine hydrochloride in a vial or ampoule.

In yet another embodiment, the vial or ampoule has about 1 ml to about 10 ml of a solution of amantadine hydrochloride, which is diluted prior to administration to the patient.

In another embodiment, the composition is in the form of a solution of amantadine hydrochloride in an infusion bag, ready to administer to a patient. In one embodiment, the infusion bag has a volume of about 50 ml to about 500 ml.

In some embodiments, the aminoadamantane derivative is administered parenterally in combination with other neuroprotective and/or anti-inflammatory compounds, in particular anti-neuroinflammatory compounds for treating the impaired neurological function, CNS disease or condition in patients with TBI.

In some embodiments, the aminoadamantane derivative alone or in combination with other neuroprotective and/or anti-inflammatory compounds is administered parenterally for cognitive improvement in the CNS disease or condition.

In some embodiments, the aminoadamantane derivative alone or in combination with other neuroprotective and/or anti-inflammatory compounds is administered parenterally for reducing neuron inflammation.

DETAILED DESCRIPTION

As used herein, a "pharmacologically effective amount" means the amount that, when administered to a human subject for treating a disease, is sufficient to effect treatment for that disease.

As used herein, the term "treating" or "treatment" of a disease includes prophylactic treatment, i.e., preventing the disease from occurring in a human subject that may be predisposed to the disease but does not yet experience or exhibit symptoms of the disease; inhibiting the disease, i.e., slowing or arresting development of the disease; palliative treatment, i.e., providing relief from the symptoms or side-effects of the disease; and causing regression of the disease.

As used herein, the term "TBI" refers to traumatic brain injury, i.e., mild as well as severe traumatic brain injury, including coma, vegetative state, minimum consciousness state and disorder of consciousness.

A "stable" composition herein means that substantially no degradation of the composition is observed after storage for at least 1 month at 40° C. at 75% relative humidity, when present as a preconcentrate. The preconcentrates of the present invention, when diluted with pharmaceutically acceptable diluents, is stable for at least 48 hours after dilution, when stored at room temperature.

Neuroprotective and/or anti-inflammatory compounds are agents that reverse some of the damage to CNS, prevent further damage and/or reduce neuroinflammation, and include immunosuppressive calcineurin inhibitors, NOS inhibitors, sigma-1 modulators, AMPA antagonists, calcium channel blockers, estrogen agonists and glycoprotein IIb/IIIa antagonists, naloxone, gangliosides, glutamate antagonists, and free-radical scavengers. In particular, neuroprotective agents include NMDA receptor antagonists, agents that enhance NMDA receptor antagonists, and agents that can reduce neuron inflammation. Neuroprotective agents are for example described by Levi et al., Curr Med Chem. 2004; 11(18):2383-97, and plants-derived agents described by Elufioye et al., Evid Based Complement Alternat Med. 2017; 2017: 3574012. Examples of neuroprotective compounds include modafinil, which may act on several receptors.

Anti-neuroinflammatory compounds act by regulating inflammatory process in the CNS, and may also have anti-oxidative and neuroprotective effect. Anti-neuroinflammatory compounds are well known in the art and include natural and synthetic compounds such as those disclosed in Shi et al., Pharmacol Res., 136:172-180 (2018); Zhou et al., Future Med Chem., 5(13):1559-71 (2013); and Shal et al., Front Pharmacol., 9:548 (2018).

The aminoadamantane derivatives that are useful in the present invention include amantadine (1-amantanamine), adapromine (1-adamantanylpropylamine), rimantadine (methyl-1-adamatanethylamine), bromantane (1-amino-2-bromophenyladamantane), memantine (3,5-dimethyl-1-adamantanamine) and derivatives thereof, as well as their pharmaceutically acceptable salts. Particularly, amantadine hydrochloride is the preferred aminoadamantane for use in the treatment of the CNS disease or condition, as described herein. In a preferred embodiment, the method comprises administration of amantadine hydrochloride to a patient with a CNS disease or condition, wherein the CNS condition is TBI.

The amantadine hydrochloride is used in a dose ranging from about 50 mg to about 500 mg, as a daily dose, preferably from about 50 mg to about 400 mg as a daily dose, more preferably about 200 mg to about 400 mg as a daily dose. The present invention involves treating TBI wherein the patient is administered a pharmacologically effective amount of amantadine hydrochloride in a single or divided dose, i.e. once daily, twice daily or three times daily. In preferred embodiments of the invention, the amantadine hydrochloride is administered at a dose of about 200 mg to about 400 mg, divided in two doses.

Parenteral administration of compositions of the invention may be performed by injection or by the insertion of an in-dwelling catheter. The composition may be administered intravenously, intraarterially, subcutaneously, intramuscularly, intracerebrally, intracerebroventricularly, or intracisternally. In certain preferred embodiments, the composition may be administered via intravenous bolus, intravenous infusion, or intra-arterial tube. The parenteral administration may be adjusted to maintain consistent levels of amantadine in the plasma or cerebrospinal fluid (CSF) of the human subject. The compositions of the invention to be administered parenterally are stable sterile injectable compositions which may contain conventional non-toxic pharmaceutically acceptable carriers, adjuvants and vehicles. The present invention also covers parenteral compositions of amantadine hydrochloride that are free of excipients and preservatives.

The parenteral compositions of the present invention may be in the form of a solution, including a liquid concentrate in a non-toxic parenterally acceptable diluent or solvent, a suspension, or may be in the form of a lyophilized preparation for reconstitution. The injectable compositions of the invention, when in the form of a solution, are preferably aqueous, clear, and display no precipitate or crystals. In some embodiments of the injectable compositions, the aminoadamantane derivatives or salts thereof, alone or in combination with other neuroprotective and anti-inflammatory compounds, may be in micelles or inclusion complexes, which can be diluted with a pharmaceutically acceptable carrier for injection to produce a thermodynamically stable solution or suspension.

In certain embodiments, a unit dose of the dry powder composition provided in an ampoule or a vial, is diluted to a total volume of 5 ml with water for injection.

When present in the form of a solution, which is the preferred dosage form, the parenteral compositions of the present invention may be in the form of a preconcentrate solution for dilution, or may be in the form of a ready-to-use infusion. When present as a preconcentrate solution for dilution, the composition is to be diluted prior to administration, using diluents that are typically used in a hospital setting, such as sterile water, Ringer's solution, isotonic sodium chloride, and isotonic dextrose. The amount of diluent used for the dilution of the preconcentrate of amantadine hydrochloride solution of the present invention depends on several factors, such as the dose required by the patient, the desired osmolality of the composition, the amount of fluid that the patient can tolerate, given that TBI patients are to be monitored carefully for the total body fluid for avoiding any increase in the intracranial pressure. In most preferred embodiments, the preconcentrate of the present invention is diluted to a volume of about 250 ml with the diluent, as described above.

The preconcentrate itself is a solution wherein the aminoadamantane derivative may be present in a concentration of from about 0.5 mg/ml to about 10 mg/ml, and preferably from about 1 mg/ml to about 5 mg/ml. The vehicle may be water for injection, a pharmaceutically acceptable alcohol such as ethanol, a mixture of water for injection and ethanol, 5% dextrose solution, 0.9% saline solution, and the like. The preconcentrate solution may contain other pharmaceutically acceptable excipients such as tonicity agents, pH adjusting agents, preservatives, buffers, antioxidants, stabilizers, chelating agents and the like.

Examples of tonicity agents that can be used in the compositions of the present invention include, but are not limited to, sodium chloride, mannitol, dextrose, potassium chloride, sodium chloride and mixtures thereof. The tonicity agents may be present in an amount so as to provide osmolality of from about 250 mOsm/kg to about 350 mOsm/kg, particularly from 280 mOsm/kg to 320 mOsm/kg. Alternatively, the desired osmolality may be achieved by diluting the composition containing amantadine hydrochloride with conventional diluents. The osmolality of amantadine hydrochloride solution in sterile water for injection was studied at various concentrations, and the same is provided in Table 1 below—

TABLE 1

| Strength of the solution of amantadine hydrochloride | Osmolality (mOsm/kg) |
| --- | --- |
| 10 mg/ml | 97 |
| 20 mg/ml | 192 |
| 30 mg/ml | 283 |
| 40 mg/ml | 369 |
| 50 mg/ml | 509 |
| 75 mg/ml | 671 |

In preferred embodiments of the present invention, the pharmaceutical composition is a solution containing amantadine hydrochloride in sterile water for injection, and is free of any excipients. Upon dilution to 250 ml with the diluents described above, the amantadine hydrochloride solution, which is ready for administration to the patient, has an osmolality that is in the range of about 275 mOsm/kg to about 350 mOsm/kg.

In some embodiments of the present invention, the pH is adjusted using a pharmaceutically acceptable buffer or pH adjusting agent, including hydrochloric acid, citric acid, lactic acid, sodium hydroxide, potassium hydroxide, triethylamine, meglumine, L-Arginine, sodium bicarbonate, citrate buffers, phosphate buffers such as sodium phosphate buffer, and mixtures thereof. The pH of the parenteral composition of the present invention that is ready for administration to the patient is from about pH 3 to about pH 9, preferably from about pH 4.5 to about pH 8.

Antimicrobial agents, preservatives, or stabilizers in bacteriostatic or fungistatic concentrations may be added to parenteral preparations packaged in multiple dose containers. Antimicrobial agents include phenols, cresols, mercurials, benzyl alcohol, chlorobutanol, methyl and propyl p-hydroxybenzoic acid esters, thimerosal, benzalkonium chloride, benzethonium chloride, boric acid, p-hydroxybenzoates, phenols, chlorinated phenolic compounds, alcohols, quarternary compounds, and mixtures thereof. The amount of preservative(s), when used, is in an amount conventional to the pharmaceutical art.

The present invention also provides a composition that is free of excipients and preservatives. In one preferred embodiment of the present invention, the pharmaceutical composition is a preconcentrate solution containing amantadine hydrochloride dissolved in water for injection, and does not contain any excipient or additive. Such a preservative-free and excipient-free composition is ideal for use in TBI patients who are on concomitant drug therapy for treating and/or controlling other symptoms, and absence of excipients ensures lack of any reactions with concomitantly administered medications. Also, use of such preservative-free, excipient-free compositions means lower load on the physiology and metabolism of the TBI patient. For example, the compositions of the present invention that are free of excipients also ensure that the administration of the composition does not impact the electrolyte balance in the patient, and there is no need to adjust the dose in patients with impaired cardiovascular and/or renal function. The amantadine hydrochloride preconcentrate solution of the present invention has a strength ranging from about 0.1 mg/ml to about 10 mg/ml. Upon dilution with a suitable diluent, as described above, the parenteral composition that is ready for administration to a patient, includes amantadine hydrochloride in a concentration ranging from about 0.1 mg/ml to about 5 mg/ml.

The compositions of the present invention are prepared by placing an amount of the aminoadamantane derivative and dissolving it in water for injection. This may be followed by adding an amount of tonicity agent(s) calculated to render the resulting composition isotonic with body fluids, adding the pH-adjusting agent and remaining amount of water necessary to bring the total volume to the desired concentration, and combining any other ingredients. The procedure is carried out from about 15° C. to about 50° C., preferably at about room temperature, and at atmospheric pressure. The resulting formulation is transferred to unit dosage containers (such as vials or bottles or ampoules or prefilled syringes) for storage prior to use. Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the aminoadamantane derivative in a pharmacologically effective amount for treatment of a CNS disease or condition in accordance with the teachings of this invention. Examples included herein below also provide details on preparing compositions of the invention that are free of excipients.

The pharmaceutical compositions of the present invention may be packaged in vials, ampoules or prefilled syringes, when they are in the form of a preconcentrate solution for dilution. The preconcentrate is then added to a diluent solution, either by withdrawing the desired volume from the vial or ampoule, or injecting the desired volume from a prefilled syringe into an infusion bag containing the desired diluent. When the composition is prepared as a ready-to-use solution, for infusion, it is packaged in infusion bags or bottles of desired volume. The headspace of the bottles may be purged with inert pharmaceutically acceptable gas to ensure stability of the solution. Alternatively, the headspace of the infusion bags and bottles may be subjected to vacuum to ensure that oxygen from the headspace is reduced to levels as low as possible. The packaging materials used are those commonly used in the pharmaceutical art, and ensure quality of the composition through its shelf life.

As is known from the literature, amantadine increases the extracellular dopamine concentration, both by increased dopamine release and through blockade of re-uptake into the presynaptic neurons. While this is helpful in improving vigilance in patients with Parkinson's disease, the increased vigilance could impact the sleep pattern in patients, and that is undesirable in TBI patients, because they need to be able to sleep at night, sleep being essential to recovery. Therefore, care needs to be taken to ensure that the amantadine plasma levels fall to a level such that the patient is able to fall asleep, and is not in an excited state during the late hours of the day. Thus, when administered as a single dose, the timing of administration needs to be adjusted carefully. When administered in divided doses, the two or more doses should be spaced out in a manner such that the amantadine plasma levels fall at the appropriate time, after the last dose, thereby ensuring that the patient is able to sleep at night. For example, when administered as a single dose, it may be administered at about noon, so that by evening the amantadine levels have fallen to those at which the patient is not in an excited state. Similarly, when administered as two divided doses, the first dose may be administered early in the morning, followed by the second dose being administered about 3 to about 5 hours after the end of the first dose, such that the second dose is completed by evening, ensuring that the amantadine plasma levels are low enough not to cause excitation. Typically, the two doses are spaced apart by at least a few hours. In some embodiments, where the aminoadamantane is dosed over multiple daily doses, the composition is infused every about 3 to about 5 hours. Each dose is itself administered over a period of time ranging from about 1 hour to about 5 hours.

It is also important to monitor the rate of administration of the parenteral composition of the present invention because in patients with CNS disease or condition, especially those with TBI, the volume of the physiological fluids may impact the intracranial pressure, and could complicate matters. Therefore, the composition is administered intravenously over a period of time, and the rate of administration is titrated such that the patient can tolerate the same. In certain embodiments, the aminoadamantane derivative is dosed at about 0.05 mg to about 100 mg per hour by continuous intravenous infusion. The present invention also relates to parenteral compositions of amantadine hydrochloride that are administered for treating a patient with TBI, wherein the composition is administered at a rate of about 10 mg/hr to about 400 mg/hr. Preferably, the parenteral composition of the present invention is administered at a rate ranging from about 10 mg/hr to about 150 mg/hr, more preferably from about 15 mg/hr to about 135 mg/hr. Infusion volumes may range from about 50 ml to about 1000 ml. As previously discussed above, the preconcentrate solution of the compositions of the present invention can be diluted with known diluent solutions to volumes ranging from about 50 ml to about 1000 ml, preferably from about 100 ml to about 500 ml, more preferably from about 100 ml to about 250 ml. In preferred embodiments, the composition contains amantadine hydrochloride in an amount ranging from about 50 mg to about 400 mg, in a volume ranging from about 1 ml to about 250 ml.

The preconcentrate solution compositions of the present invention are tested for stability to ensure that they are safe and efficacious over the entire shelf life of the composition. Also, the preconcentrate solutions are stable upon dilution with the diluent solutions, such that there is no precipitation or degradation of the aminoadamantane derivative, for at least 48 hours after dilution, when stored at room temperature. Stability parameters typically checked for are those provided in Example 2 below.

The aminoadamantane derivative containing parenteral compositions of the present invention may be administered to patients with CNS disease or condition over a period of 12 hours to about 16 weeks, or until such time that the patient shows improvement in the symptoms. Such improvement would be patient specific and would be defined by the treating physician.

The present invention provides a composition of amantadine hydrochloride in the form of a solution for parenteral administration to a patient with TBI, such that about 100 mg to about 400 mg of amantadine hydrochloride is administered in multiple or divided doses, wherein each dose is present in a volume of about 250 ml, and is administered over a period of about 1 hour to about 3 hours, and wherein the multiple or divided doses are separated by about 3 hours to about 5 hours.

In certain embodiments of the present invention, the injection concentrate of the aminoadamantane derivative, salt thereof and/or other neuroprotective and anti-inflammatory compound is diluted in an infusion bag containing water for injection or any commonly available intravenous infusion solution. In certain embodiments, the infusion set and bag may be covered with ultraviolet light (UV) protective bags to protect the aminoadamantane derivative, salt thereof and/or other neuroprotective and anti-inflammatory compound from photo-degradation.

A continuous intravenous infusion of the compositions of the invention from a single bag or bottle is a convenient way to administer an effective concentration of an aminoadamantane derivative, salt thereof and optionally other neuroprotective and anti-inflammatory compound to an unconscious patient or to a patient having difficulty in swallowing oral dosage forms. In certain embodiments of the present invention, the solution of an aminoadamantane derivative, salt thereof and optionally other neuroprotective and anti-inflammatory compound may be continuously infused over a period of from about 12 hours to about 3 weeks, or more.

Other neuroprotective and anti-inflammatory compounds are used in conventional amounts and doses.

The diluent or solvent may be aqueous, oil based, or an organic solvent. Selection of a suitable diluent or solvent is based on the solubility of the aminoadamantane derivative, salts thereof, and other neuroprotective and anti-inflammatory compounds, if used, in the diluent or solvent, the degree to which the diluent or solvent is miscible in water and the tolerability of the diluent or solvent. Oil based diluent may be a sterile fixed oils, including cottonseed oil, corn oil, sesame oil and peanut oil, synthetic mono or diglycerides, or fatty acids such as oleic acid. Examples of organic solvents include alcohols, such as ethanol, glycols, glycerin, propylene glycol, various polyethylene glycols, and dimethyl isosorbide (DMI).

The compositions of the invention may be prepared according to methods known in the art using suitable suspending, dispersing or wetting agents and surfactants, solubilizing agents, or emulsifying agents. Suspending and dispersing agents include sodium carboxymethylcelluose, hydroxypropyl methylcellulose and polyvinylpyrrolidone. Emulsifying agents include phospholipid, polyethylene glycol, and polysorbate 80. Solubilizing agents include glucose, polyethylene glycol, polypropylene glycol and mixtures thereof. Surfactants include polyoxyethylene compounds, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters. Water-miscible surfactant molecules can solubilize select poorly water-soluble aminoadamantane derivatives, salts thereof, and/or other neuroprotective and anti-inflammatory compounds, if used. Surfactants can also self-assemble to form micelles once the surfactant monomer concentration reaches the critical micelle concentration.

In certain embodiments, the aminoadamantane derivative, salt thereof and/or other neuroprotective and anti-inflammatory compound, is contained in micelles or as a nanoemulsion in the injectable composition. Micellar or nanoemulsion compositions generally contain an aminoadamantane derivative and/or other neuroprotective and anti-inflammatory compound, a hydrophilic surfactant or emulsifier such as polysorbate 80, an organic solvent, and a pharmaceutically acceptable aqueous carrier. Micelles or nano-emulsions of the clear solution of an aminoadamantane derivative, salt thereof and/or other neuroprotective and anti-inflammatory compound may be obtained by dissolving it in a small amount of organic solvent or oil, optionally the hydrophilic surfactant or emulsifier, and then combining the other ingredients.

In certain embodiments, the composition is a cyclodextrin inclusion complex. Suitable cyclodextrins include a β-cyclodextrin such as hydroxy-propyl-β-cyclodextrin, and a β-cyclodextrin comprising one or more hydroxybutyl sulfonate moieties such as sulfobutyl-ether-β-cyclodextrin, α-cyclodextrins, and γ-cyclodextrins. A suitable amount of aminoadamantane derivative and/or other neuroprotective and anti-inflammatory compound together with a hydrophilic surfactant may be admixed into a suitable amount of a cyclodextrin in water for a sufficient period of time to form a stable inclusion complex.

EXAMPLES

Example 1

| Ingredient | Concentration (mg/mL) |
| --- | --- |
| Amantadine Hydrochloride | 50 |
| Sterile Water for Injection | QS to 1 mL |

Amantadine Hydrochloride Intravenous Solution, 50 mg/mL, is a sterile, particle free solution filled into 10-mL vials with above composition. The drug product consists of only the active pharmaceutical ingredient, Amantadine Hydrochloride, USP, and Sterile Water for Injection, USP. The container closure system consists of a vial, stopper, and flip-off seal.

Amantadine Hydrochloride Intravenous Solution, 50 mg/mL can be diluted with 0.9% Sodium Chloride for Injection, USP in an IV bag and administered directly to a patient.

The product was manufactured with below steps with a precaution of light exposure.
1. Add total amount of Amantadine Hydrochloride to a predetermined amount of sterile water for injection, USP (SWFI, USP) in glass carboy.
2. Mix them with magnetic stirrer until all drug dissolved.
3. Make final dilution with SWFI, USP up to concentration of 50 mg/ml Amantadine Hydrochloride and mix with a magnetic stirrer for a minimum of 5-10 minutes.
4. Filter whole bulk with prefilter and 0.22-μm sterile membrane filter in series.
5. Fill each sterile vial with 10 ml of the above solution, and stopper vial.
6. Crimp the seals on the vials.
7. Sterilize the vials via autoclave.

The osmolality of the solution obtained by the process of Example 1 was 483 mOsm/kg.

Example 2

The product obtained in Example 1 above was subjected to stability study.

| Test | Initial | 1M 25° C./ 60% RH | 1M 40° C./ 75% RH |
| --- | --- | --- | --- |
| Appearance | Clear, colorless solution, essentially free of visible particulates | Clear, colorless solution, essentially free of visible particulates | Clear, colorless solution, essentially free of visible particulates |
| pH | 7.3 | 5.8 | 5.8 |
| Assay | 99.40% | 99.60% | 99.90% |
| Related Substances | Not Detected | Not Detected | Not Detected |
| Particulate Matter for SVP (small volume parenterals) | ≥10 μm-133 particles ≥25 μm- 97 particles | ≥10 μm-15 particles ≥25 μm- 1 particles | ≥10 μm-21 particles ≥25 μm- 2 particles |

Example 3

A study was conducted using Amantadine Hydrochloride Solution in 10 healthy subjects. In one period of the study, a single 50 mg dose of amantadine hydrochloride was administered as 1 mL×50 mg/mL, diluted into 250 mL of sterile intravenous saline solution, infused over 180 minutes following an overnight fast of at least 10 hours (Treatment A). In the other study period, a single 200 mg oral dose of amantadine hydrochloride as 2×100 mg capsules were administered to subjects following an overnight fast of at least 10 hours (Treatment B).

For Treatment A, plasma concentrations of amantadine increased over the 3-hour duration of the infusion and, in some subjects, they continued to increase for approximately 1 hour following the end of the infusion to a mean $C_{max}$ of 142 ng/mL at a median $T_{max}$ of 4.0 hours (mean: 4.1 hours). Concentrations declined thereafter with a mean apparent first-order elimination half-life ($T_{1/2}$) of 14.0 hours. The increase in plasma concentrations following discontinuation of the infusion may have resulted from transient release of drug from red blood cells to plasma.

For Treatment B, plasma concentrations of amantadine increased to a mean $C_{max}$ of 643 ng/mL at a median $T_{max}$ of 2.8 hours (mean: 3.6 hours). Concentrations declined thereafter with a mean $T_{1/2}$ of 14.6 hours.

Peak and total plasma exposures of amantadine following the infusion were approximately 5-fold (80%) lower than those from the reference oral dose despite a 4-fold lower dose, as indicated by least-squares geometric mean (LSGM) test-to-reference (A/B) ratios of 20-22% for the AUC ($AUC_{0-24}$, $AUC_{0-t}$ and $AUC_{0-\infty}$) and $C_{max}$ parameters.

The bioavailability of the oral capsule was estimated as 122%, as determined from the LSGM A/B ratio of the intravenous plasma clearance ($CL_{IV}$) to apparent oral plasma clearance ($CL_{IV}/F$). That this estimate is more than 100% indicates that a single oral dose of 200 mg provides a greater than proportional increase in plasma concentrations compared to a 50 mg oral dose (i.e., exhibits non-linear pharmacokinetics at an oral dose of 200 mg), and likely explains why the amantadine intravenous concentrations from the 50 mg dose were approximately 5-fold instead of a maximum of 4-fold lower relative to the reference 200 mg oral dose.

The invention claimed is:

1. A method of treating traumatic brain injury (TBI) in a human subject comprising intravenously administering a composition consisting of a pharmacologically effective amount of amantadine or a pharmaceutically acceptable salt thereof in sterile water and wherein the composition is free of any other excipients, the composition has a volume of about 100 ml to about 1000 ml and the composition is administered once or twice daily at a daily dose of about 200 mg to about 400 mg amantadine or a pharmaceutically acceptable salt thereof at a rate of about 15 mg/hr to about 135 mg/hr.

2. The method of claim 1, wherein the composition comprises amantadine hydrochloride.

3. The method of claim 1, wherein the traumatic brain injury is mild TBI.

4. The method of claim 1, wherein the traumatic brain injury is severe TBI.

5. The method of claim 4, wherein the severe TBI results in coma, vegetative state, minimum consciousness state or disorder of consciousness.

6. The method of claim 1, wherein the traumatic brain injury is caused by a stroke or an accident.

7. The method of claim 1, wherein the composition is in the form of a solution in a vial, ampule, an infusion bag or a prefilled syringe.

8. The method of claim 2, wherein the composition contains about 0.1 mg/ml to about 10 mg/ml of amantadine hydrochloride.

9. The method of claim 1, wherein the composition is administered in combination with other neuroprotective and/or anti-inflammatory compounds.

10. The method of claim 9, wherein the neuroprotective and/or anti-inflammatory compound is selected from the group consisting of an NMDA receptor antagonist, an agent that enhances NMDA receptor antagonists, and an agent that can reduce neuron inflammation.

11. The method of claim 9, wherein the neuroprotective and/or anti-inflammatory compound is selected from modafinil, carbidopa, levodopa, methylphenidate, memantine and mixtures thereof.

12. A method of treating mild or severe traumatic brain injury (TBI) in a human subject comprising intravenously administering a composition consisting of a daily dosage of about 200 mg to about 400 mg of amantadine hydrochloride in sterile water, wherein the composition is administered at a rate of about 15 mg/hr to about 135 mg/hr of amantadine hydrochloride, the composition has a volume of about 100 ml to about 1000 ml, and the composition is administered once or twice daily.

13. The method of claim 12, wherein the composition has a volume of about 250 ml and contains about 0.1 mg/ml to about 10 mg/ml of amantadine hydrochloride.

14. The method of claim 12, wherein the composition is administered intravenously.

15. The method of claim 12, wherein the composition is in the form of a solution in a vial, ampule, an infusion bag or a prefilled syringe.

16. The method of claim 12, wherein the composition is administered in combination with other neuroprotective and/or anti-inflammatory compounds.

17. The method of claim 16, wherein the neuroprotective and/or anti-inflammatory compound is selected from the group consisting of an NMDA receptor antagonist, an agent that enhances NMDA receptor antagonists, and an agent that can reduce neuron inflammation.

18. The method of claim 17, wherein the neuroprotective and/or anti-inflammatory compound is selected from modafinil, carbidopa, levodopa, methylphenidate, memantine and mixtures thereof.

19. The method of claim 12, wherein the composition consisting of about 200 mg to about 400 mg of amantadine hydrochloride in sterile water is administered once daily at a rate of about 15 mg/hr to about 135 mg/hr of amantadine hydrochloride.

20. The method of claim 12, the method comprising: (i) a first period of administrating of the composition consisting of about 200 mg to about 400 mg of amantadine hydrochloride in sterile water at a rate of about 15 mg/hr to about 135 mg/hr of amantadine hydrochloride, (ii) followed by a second period without administration of amantadine hydrochloride, and (iii) followed by a third period of administrating of the composition consisting of about 200 mg to about 400 mg of amantadine hydrochloride in sterile water at a rate of about 15 mg/hr to about 135 mg/hr of amantadine hydrochloride, whereby the administration comprises twice daily administration of the composition.

* * * * *